United States Patent
Kang et al.

(10) Patent No.: US 10,251,559 B2
(45) Date of Patent: Apr. 9, 2019

(54) LASER-INDUCED ULTRASONIC WAVE APPARATUS AND METHOD

(71) Applicant: SAMSUNG ELECTRONICS CO., LTD., Suwon-si, Gyeonggi-do (KR)

(72) Inventors: Sung-chan Kang, Hwaseong-si (KR); Woon-bae Kim, Seoul (KR); Jong-seok Kim, Hwaseong-si (KR); Yong-seop Yoon, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 361 days.

(21) Appl. No.: 13/886,792

(22) Filed: May 3, 2013

(65) Prior Publication Data

US 2013/0303909 A1    Nov. 14, 2013

(30) Foreign Application Priority Data

May 3, 2012  (KR) .................. 10-2012-0047127

(51) Int. Cl.
*A61B 5/00*    (2006.01)
*G01N 29/00*    (2006.01)
(Continued)

(52) U.S. Cl.
CPC ....... *A61B 5/0095* (2013.01); *G01N 29/2418* (2013.01); *G10K 15/046* (2013.01);
(Continued)

(58) Field of Classification Search
CPC combination set(s) only.
See application file for complete search history.

(56) References Cited

U.S. PATENT DOCUMENTS 4,512,197 A * 4/1985 von Gutfeld ...... G01N 29/2418
                                                          73/601
4,513,384 A * 4/1985 Rosencwaig .................. 702/170
(Continued)

FOREIGN PATENT DOCUMENTS

JP    2006-208050    8/2006
JP    2010-167167    8/2010
(Continued)

OTHER PUBLICATIONS

Hsieh et al. "All-optical scanhead for ultrasound and photoacoustic dual-modality imaging", Optics Express. Jan. 16, 2012. pp. 1588-1596. vol. 20, No. 2.*
(Continued)

*Primary Examiner* — Michael Carey
*Assistant Examiner* — Don N Ho
(74) *Attorney, Agent, or Firm* — Harness, Dickey & Pierce, P.L.C.

(57) ABSTRACT

Laser-induced ultrasonic wave apparatuses and methods of generating images using the same. The laser-induced ultrasonic wave apparatus includes a laser source which irradiates a laser beam to a target object and a thermoelastic material; a thermoelastic material which converts the laser beam to a first ultrasonic wave and irradiates the first ultrasonic wave to the target object; and a receiving unit which receives an echo acoustic wave of the first ultrasonic wave and receives a second ultrasonic wave generated by the target object due to the laser beam.

28 Claims, 9 Drawing Sheets

(51) Int. Cl.
  *G10K 15/00* (2006.01)
  *G01N 29/24* (2006.01)
  *G10K 15/04* (2006.01)
  *A61B 8/00* (2006.01)

(52) U.S. Cl.
  CPC .......... *A61B 5/0035* (2013.01); *A61B 8/4483* (2013.01); *G01N 2291/02475* (2013.01)

(56) References Cited

U.S. PATENT DOCUMENTS

| | | | |
|---|---|---|---|
| 5,615,675 A * | 4/1997 | O'Donnell | G01N 29/0681 600/425 |
| 5,840,023 A | 11/1998 | Oraevsky et al. | |
| 6,979,292 B2 | 12/2005 | Kanayama et al. | |
| 8,059,923 B2 * | 11/2011 | Bates et al. | 385/7 |
| 9,351,705 B2 * | 5/2016 | Wang | A61B 5/0062 |
| 2001/0055435 A1 | 12/2001 | Biagi et al. | |
| 2004/0039379 A1 * | 2/2004 | Viator | A61B 18/203 606/9 |
| 2005/0131289 A1 * | 6/2005 | Aharoni | A61B 5/02007 600/407 |
| 2007/0255141 A1 * | 11/2007 | Esenaliev et al. | 600/475 |
| 2008/0071172 A1 * | 3/2008 | Bruck et al. | 600/438 |
| 2010/0041987 A1 * | 2/2010 | Manohar et al. | 600/437 |
| 2010/0049044 A1 * | 2/2010 | Burcher | 600/437 |
| 2010/0154549 A1 | 6/2010 | Fomitchov | |
| 2010/0242612 A1 * | 9/2010 | Sano | B06B 1/0292 73/632 |
| 2011/0021924 A1 | 1/2011 | Sethuraman et al. | |
| 2011/0048135 A1 * | 3/2011 | Caron | 73/633 |
| 2011/0303015 A1 | 12/2011 | Ichihara et al. | |
| 2011/0306857 A1 * | 12/2011 | Razansky et al. | 600/317 |
| 2012/0065490 A1 * | 3/2012 | Zharov et al. | 600/407 |
| 2013/0190594 A1 * | 7/2013 | Oraevsky | A61B 5/0095 600/407 |
| 2013/0190595 A1 * | 7/2013 | Oraevsky | A61B 5/0095 600/407 |
| 2016/0051149 A1 * | 2/2016 | Viator | A61B 5/445 600/407 |

FOREIGN PATENT DOCUMENTS

| | | |
|---|---|---|
| JP | 2011-229660 | 11/2011 |
| KR | 2005-0003948 A | 1/2005 |
| WO | WO 2009158146 A2 * | 12/2009 |
| WO | WO-2011/070985 A1 | 6/2011 |
| WO | 2011/135821 | 11/2011 |

OTHER PUBLICATIONS

International Search Report dated Aug. 23, 2013 in related International Application No. PCT/KR2013/003876.

R.M. White, "Generation of Elastic Waves by Transient Surface Heating", Journal of Applied Physics/ (vol. 34, Issue 12) Jun. 28, 1962.

Seung H. Ko., "Laser induced short plane acoustic wave focusing in water", Applied Physics Letters 91, 051128 (Jun. 4, 2007).

Takashi Buma, "A High-Frequency, 2-D Array Element Using Thermoelastic Expansion in PDMS", IEEE Transactions on Ultrasonics, Ferroelectrics, and Frequency Control, vol. 50, No. 9, Sep. 2003.

Bao-Yu Hsieh et al., "All-Optical Generation and Detection of Acoustic Waves for Intravascular Ultrasound and Photoacoustic Imaging," Ultrasonics Symposium (IUS), 2011 IEEE International, IEEE, Oct. 18, 2011, pp. 1175-1178.

Bao-Yu Hsieh, et al. "All-optical scanhead for ultrasound and photoacoustic dual-modality imaging," Nucl. Eng. Des. Eur. Phys. J. Spec. Top. IEEE Trans. Ultrason. Ferroelectr. Freq. Control J. Biomed. Opt. J. Biomed. Opt. J. Biomed. Opt. IEEE Trans. Ultrason. Ferroelectr. Freq. Control Appl. Phys. Lett. Appl. Phys. Lett. Appl. Phys. Lett. Appl. Phy., Jan. 1, 2002, pp. 151-161.

European Patent Office Extended Search Report dated Dec. 21, 2015, Application No. 13785011.1-1657/2844149.

Jan. 4, 2016, Chinese Office Action issued in corresponding Chinese Application No. 201380026661.5 (with English-language translation).

Korean Office Action dated Oct. 22, 2018 for corresponding Korean Application No. 10-2012-0047127.

* cited by examiner

LASER-INDUCED ULTRASONIC WAVE APPARATUS AND METHOD

CROSS-REFERENCE TO RELATED APPLICATIONS

This application claims the benefit of Korean Patent Application No. 10-2012-0047127, filed on May 3, 2012, in the Korean Intellectual Property Office, the disclosure of which is incorporated herein in its entirety by reference.

BACKGROUND

1. Field

One or more embodiments relate to laser-induced ultrasonic wave apparatuses and methods, including laser-induced ultrasonic wave apparatuses and methods generating one or more images.

2. Description of the Related Art

When a laser beam irradiates a liquid material or a solid material, the liquid or solid materials respectively absorbs light energy, and thus, heat energy becomes instantly generated. This generation of heat also generates acoustic waves, e.g., ultrasonic waves, due to a thermoelastic phenomenon. Here, respective absorptances and thermoelastic coefficients for different materials may also vary with respect to light wavelengths of light energy irradiating the respective materials. Thus, when different materials are irradiated with the same light energy, ultrasonic waves of different pressure magnitudes may be generated by the respectively different materials. Such ultrasonic waves that may be generated can be used for analysis of select materials, non-destructive diagnoses, photoacoustic tomography, etc.

Particularly, photoacoustic tomography may embody functional images that may be helpful for diagnoses that rely on a functional analysis of the different absorptances of tissues within the human body according to the light wavelengths of the light energy irradiating such tissues.

However, though such respective functional images or photoacoustic images may be generated, e.g., when a particular tissue is irradiated by light energy, an acoustic image or anatomical image for acoustical analysis is not generated based on the light energy irradiating the particular tissue or multiple tissues because pressure magnitudes of acoustic waves generated from the irradiation of only select tissues may be measurable, reliable, or available for acoustical analysis. This is because most materials making up the human body have low light energy absorptances, and thus, except for particular tissues like blood vessels that have relatively larger light energy absorptances, the pressure magnitudes of acoustic waves generated for such low light energy absorptance tissues are relatively very small.

Accordingly, it is difficult to distinguish between different low light energy absorptance tissues when they generate respectively small pressure magnitude acoustic waves, especially considering detection resolutions and potential substantial similarities between the relatively smaller pressure magnitude acoustic waves generated by different low light energy absorptance tissues. Therefore, it is difficult to generate anatomical images based on the thermoelastic phenomenon that can be used in an acoustical diagnosis, e.g., an ultrasonic image based diagnosis, so only functional images or photoacoustic images are generated by light energy irradiated, e.g., direct irradiation, to tissues in a human body.

Therefore, for a diagnosis that is based on both the functional analysis and the anatomical analysis, it is necessary to independently, i.e., using different acoustic generating devices or elements and techniques, generate the photoacoustic tomography image for the functional analysis and an anatomical image for anatomical analysis.

The anatomical image is typically based on acoustic waves, e.g., an ultrasound ultrasonic waves, generated by a piezoelectric device that are transmitted to, and reflected from, tissues in the human body. The anatomical image can be a typical ultrasound image. However, when piezoelectric devices are used to generate the ultrasonic waves, characteristics of the generated ultrasonic waves, such as center frequency and bandwidth, are fixed because a center frequency and bandwidth of a generated ultrasonic wave are defined by the thickness of the piezoelectric device, which is fixed. Accordingly, separate piezoelectric device probes are necessary for generating respective ultrasonic waves with different center frequencies and bandwidths, e.g., for respectively different diagnosis regions.

SUMMARY

One or more embodiments include apparatuses and methods for simultaneously obtaining images for anatomical analysis and images for functional analysis by using laser-induced ultrasonic waves.

One or more embodiments include a laser-induced ultrasonic wave apparatus, the apparatus including a laser source to generate a laser beam and to respectively irradiate a target object and a thermoelastic material with the generated laser beam, the thermoelastic material to generate a first acoustic wave based upon the irradiation of the thermoelastic material by the laser beam, and to transmit the first acoustic wave to the target object, and a receiving unit to receive and transduce an echo acoustic wave of the first acoustic wave, as reflected from the target object, and receive and transduce a second acoustic wave generated by the irradiation of the target object by the laser beam.

One or more embodiments include a laser-induced ultrasonic wave method, the method including generating a laser beam and irradiating a target object and a thermoelastic material with the generated laser beam, receiving and transducing an echo acoustic wave, from the target object, as a reflection of a first acoustic wave transmitted to the target object from the thermoelastic material upon the thermoelastic material being irradiated by the laser beam, and receiving and transducing a second acoustic wave transmitted from the target object upon the target object being irradiated by the laser beam.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
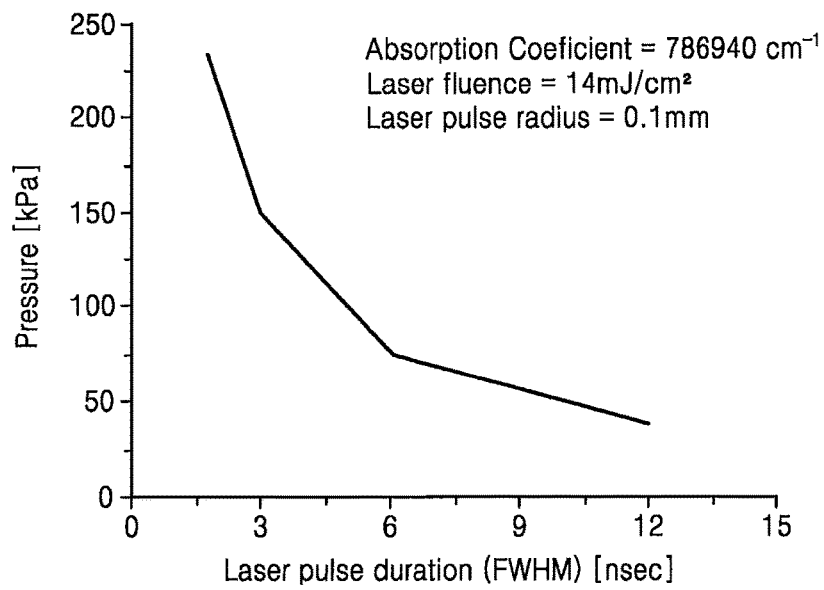
FIG. 1A is a graph illustrating pressure magnitudes of laser-induced acoustic waves according to a selectively changed pulse width of a laser beam, according to one or more embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. In addition, expressions such as "at least one of," when preceding a list of elements, modify the entire list of elements and do not modify the individual elements of the list.

As noted above, and in one or more embodiments, photoacoustic tomography may embody functional images that may be helpful for a diagnosis by relying on the different absorptances of tissues in the human body with respect to the same or different light wavelengths. However, many materials making up the human body have low light energy absorptances, and thus the pressure magnitudes of acoustic waves generated for such low light energy absorptance tissues may be very small, e.g., compared to tissues that have higher light energy absorptances, such as blood vessels, as only an example. Therefore, it may be difficult to generate anatomical images for such low energy absorptance tissues that can be used in an ultrasonic diagnosis. Accordingly, in one or more embodiments a combination of a photoacoustic tomography image for functional analysis and an image for anatomical analysis for a diagnosis may be made available, and in one or more embodiments such separate images may be made available using a single light energy source, and may be obtained simultaneously.

According to one or more embodiments, a laser-induced ultrasonic wave apparatus may be a diagnosis apparatus for determining whether a tumor has formed in a patient's body, that is, a target object, by using ultrasonic waves that are laser-induced by a laser. In one or more embodiments, a pulse laser may be employed. Furthermore, as only an example and depending on embodiment, a pulse width of the laser beam may differently be nano-sized or pico-sized, i.e., respectively on the order of $10^{-9}$ seconds or $10^{-12}$ seconds.

As defined herein, a laser-induced acoustic wave is generated as energy of a laser beam, absorbed by a thermoelastic material, is converted to pressure. When a laser beam having an energy density ($l(x, y, z, t)$) irradiates a thermoelastic material, the thermoelastic material may absorb heat H as shown in the below Equation 1, as only an example.

$$H = (1-R) \cdot I \cdot \mu e^{\mu z} \qquad \text{Equation 1:}$$

Here, R denotes a reflection coefficient of a thermoelastic material at a particular light wavelength, μ denotes an absorption coefficient of the thermoelastic material at a particular wavelength, and z denotes distance in a direction perpendicular to a surface of the thermoelastic material relative to the laser.

Furthermore, a change of temperature T may occur at the thermoelastic material as shown in the below Equation 2, as only an example, and, due to the change of temperature T, a volume V of the thermoelastic material may change as shown in the below Equation 3, also as only an example.

$$\frac{k}{C^2}\frac{\partial^2 T}{\partial t^2}\rho C_P \frac{\partial T}{\partial t} = \nabla(k \cdot \nabla T) + H \qquad \text{Equation 2}$$

$$\frac{\partial^2}{\partial t^2}\left(\frac{dV}{V}\right) = \beta \frac{\partial^2 T}{\partial t^2} \qquad \text{Equation 3}$$

Here, k denotes thermal conductivity, C denotes heat propagation speed, p denotes density of the thermoelastic material, Cp denotes specific heat of the thermoelastic material, and β denotes a corresponding thermal coefficient with respect to volume expansion.

As a result, an acoustic wave having a pressure P, such as shown in the below Equation 4, as only an example, may be generated by the change of the volume V of the thermoelastic material.

$$\frac{1}{\rho}\left(\nabla^2 - \frac{1}{v_s^2}\frac{\partial^2}{\partial t^2}\right)P = -\frac{\partial^2}{\partial t^2}\left(\frac{dV}{V}\right) \qquad \text{Equation 4}$$

Here, $v_s$ denotes velocity of the acoustic wave.

Figure 1B:
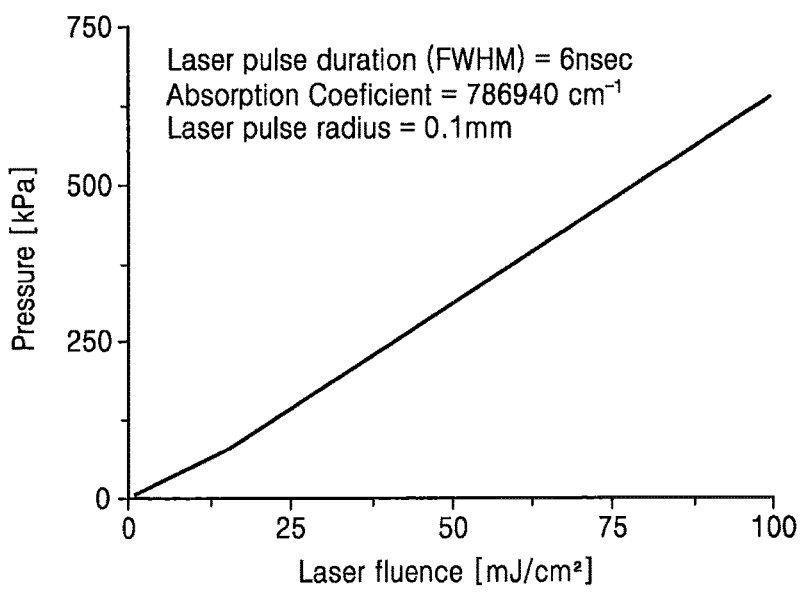
FIG. 1B is a graph illustrating pressure magnitudes of laser-induced acoustic waves according to a selectively changed pulse fluence of a laser beam, according to one or more embodiments.
Figure 1C:
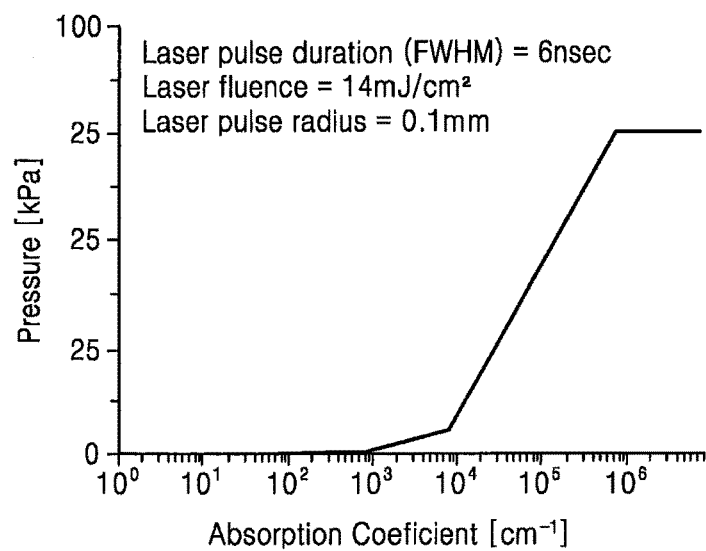
FIG. 1C is a graph illustrating pressure magnitudes of laser-induced acoustic waves according to respective absorption coefficients of materials to which a laser beam has been irradiated, according to one or more embodiments.
Figure 1D:
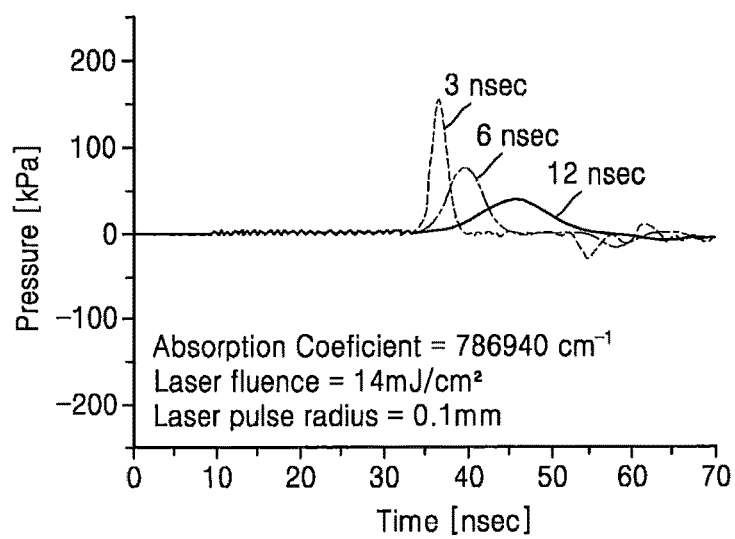
FIG. 1D is a graph illustrating pressure magnitudes and wavelengths of laser-induced acoustic waves according to a selectively changed pulse width of a laser beam in time, according to one or more embodiments.

According to one or more embodiments, FIG. 1A is a graph illustrating example different pressure magnitudes of laser-induced acoustic waves according to a selectively changed pulse width of a laser beam, e.g., incident on a thermoelastic material, FIG. 1B is a graph illustrating example different pressure magnitudes of laser-induced acoustic waves according to a selectively changed pulse fluence of a laser beam, e.g., incident on the thermoelastic material, FIG. 1C is a graph illustrating example different pressure magnitudes of laser-induced acoustic waves according to respective absorption coefficients of materials to which a laser beam may be irradiated, and FIG. 1D is a graph illustrating example different pressure magnitudes and wavelengths of respective laser-induced acoustic waves according to several respective selectively changed pulse widths of a laser beams in time, according to one or more embodiments.

FIG. 1A demonstrates at least that the smaller the pulse width of a laser beam is, the larger the pressure magnitude of a laser-induced acoustic wave becomes, FIG. 1B demonstrates at least that the greater the fluence of a laser beam is, the larger the pressure magnitude of a laser-induced acoustic wave becomes, FIG. 1C demonstrates at least that the greater the absorption coefficient of a material to which a laser beam is irradiated, the larger the pressure magnitude of a laser-induced acoustic wave becomes, and FIG. 1D demonstrates changes in wavelength of the laser-induced acoustic wave according to pulse widths of a laser beam. In addition, as the pulse width of an acoustic wave is controlled to increase, the wavelength of an acoustic wave increases, and thus a center frequency and bandwidth of the acoustic wave may be changed. FIGS. 1A-1D represent characteristics of laser-induced acoustic waves generated by either of the laser beam irradiating a thermoelastic material, e.g., the thermoelastic material layer illustrated in FIG. 3, or the laser beam directly irradiating a material whose photoacoustic image is desired, such as the target object illustrated in FIG. 3, for example.

Therefore, when a pulse laser irradiates a tissue in a body, e.g., a human body, (referred to hereinafter as the 'target object'), the target object generates an acoustic wave due to a thermoelastic phenomenon. Accordingly, the pressure magnitude of this generated acoustic wave may vary according to a pulse width of a laser beam, a pulse fluence of a laser beam, a laser absorption coefficient of the target object, a laser reflection coefficient, specific heat, a thermal expansion coefficient of a target object, velocity of the acoustic wave, etc., as only examples. In addition, since different center frequencies of the first acoustic wave may be desired for different target objects or regions in the body, different center frequencies of the first acoustic wave may be selectively changed by changing characteristics of the laser beam.

Therefore, when pulse laser beams irradiate target objects, acoustic waves having different pressure magnitudes are generated depending on a type of the target object being irradiated. Particularly, an acoustic wave generated by a target object may be an ultrasonic wave. Thus, a pulse laser beam having a known pulse width and a known pulse fluence for generating an ultrasonic wave from a target object may be used to generate an image or determine the type of the object. The type of the object may be that of an expected tissue type, or represent a type of object that is different from the expected tissue type, e.g., demonstrating a lesion or tumor. Such determination of expected type or non-expected type may be made based upon comparisons of characteristics of the received acoustic wave transmitted by the object that is being irradiated, such as whether the bandwidth or wavelength of the received acoustic wave corresponds to an expected relationship between the expected absorption coefficient of the object and the known pulse width, fluence, and frequency of the laser beam.

Furthermore, when a pulse laser beam irradiates to a thermoelastic material, since the thermoelastic material has a known high laser absorption coefficient, the thermoelastic material generates an acoustic wave of several atmospheric pressures. Furthermore, an acoustic wave generated by the thermoelastic material may be an ultrasonic wave. In other words, a pulse laser beam having a selectively changed pulse width and/or selectively changed pulse fluence for generating an ultrasonic wave from the thermoelastic material may be used. According to one or more embodiments, an anatomical image equivalent to that of a conventional ultrasonic wave diagnosis apparatus may be obtained by transmitting an ultrasound wave generated by, a thermoelastic material to a target object.

Figure 2A:
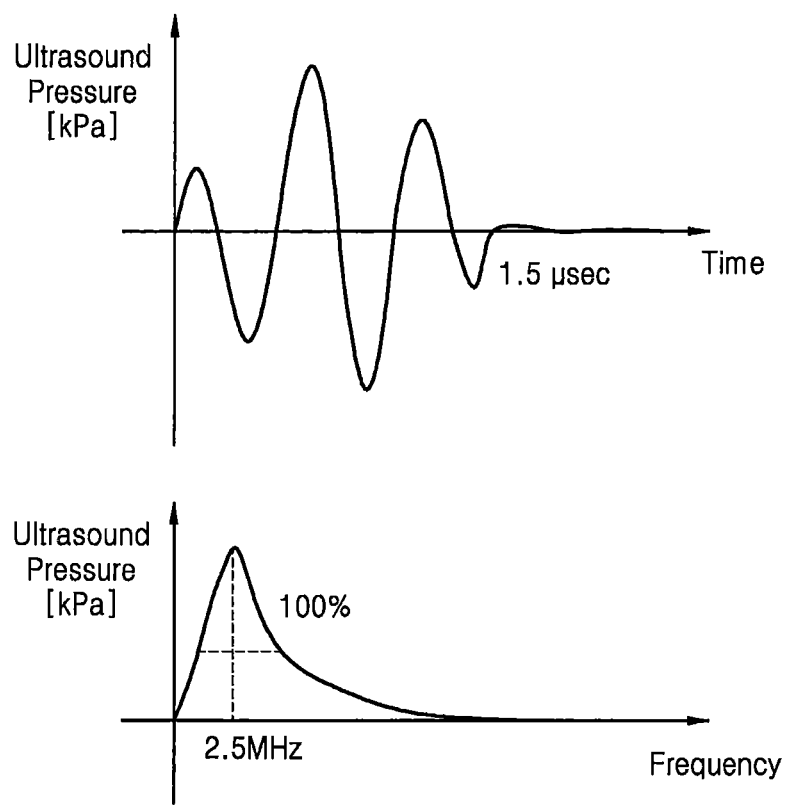
FIG. 2A is a graph illustrating acoustic pressure magnitudes of an ultrasound wave, generated by a piezoelectric device, according to time and frequency.
Figure 2B:
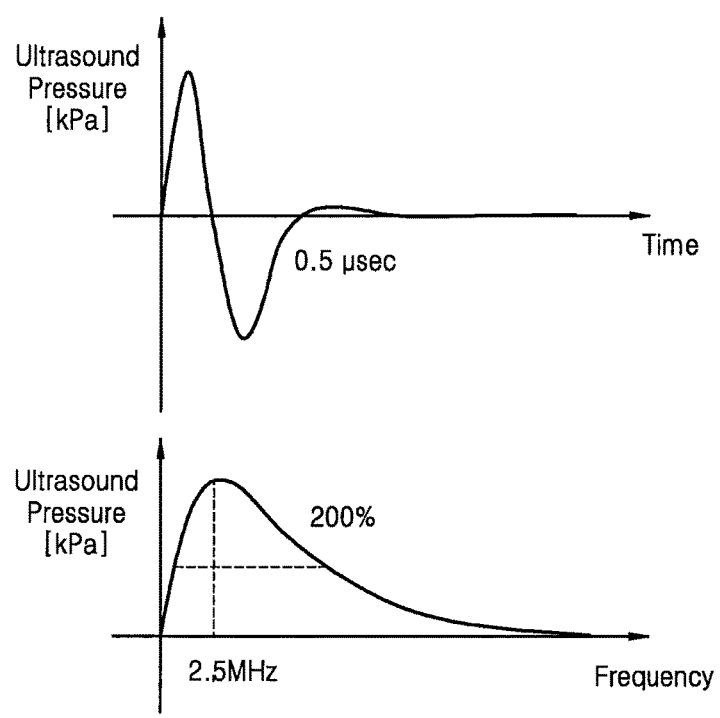
FIG. 2B is a graph illustrating example acoustic pressure magnitudes of an ultrasound wave, generated by a thermoelastic material layer as a pulse laser beam is irradiated thereto, according to time and frequency, according to one or more embodiments.

FIG. 2A is a graph illustrating changes in sound pressure magnitudes of an ultrasound wave, which is generated by a conventional piezoelectric device, according to time and frequency, and FIG. 2B is a graph showing sound pressure magnitudes of an ultrasound wave, which is generated by irradiating a thermoelastic material with a pulse laser beam to, according to time and frequency.

As shown in FIGS. 2A and 2B, even if ultrasonic waves in the same center frequency band could be generated by a conventional piezoelectric device approach and a thermoelastic material according to one or more embodiments, a wavelength of the ultrasonic wave generated by the thermoelastic material is relatively short as compared to that of the ultrasonic wave generated by the piezoelectric device. Therefore, axial-direction resolution may be improved by using an ultrasonic wave generated by a thermoelastic material. In addition, such a conventional piezoelectric device would only generate ultrasonic waves with a fixed center frequency band, thereby requiring plural different piezoelectric devices to generate respectively different ultrasonic waves having different center frequencies. Rather, according to one or more embodiments, different ultrasonic waves may be generated from irradiation of laser beams with different selected characteristics from a same laser, so the center frequencies of the respective ultrasonic waves generated by the irradiated thermoelastic material can be changed as desired, e.g., as desired by a user or through automatic selection.

Figure 3:
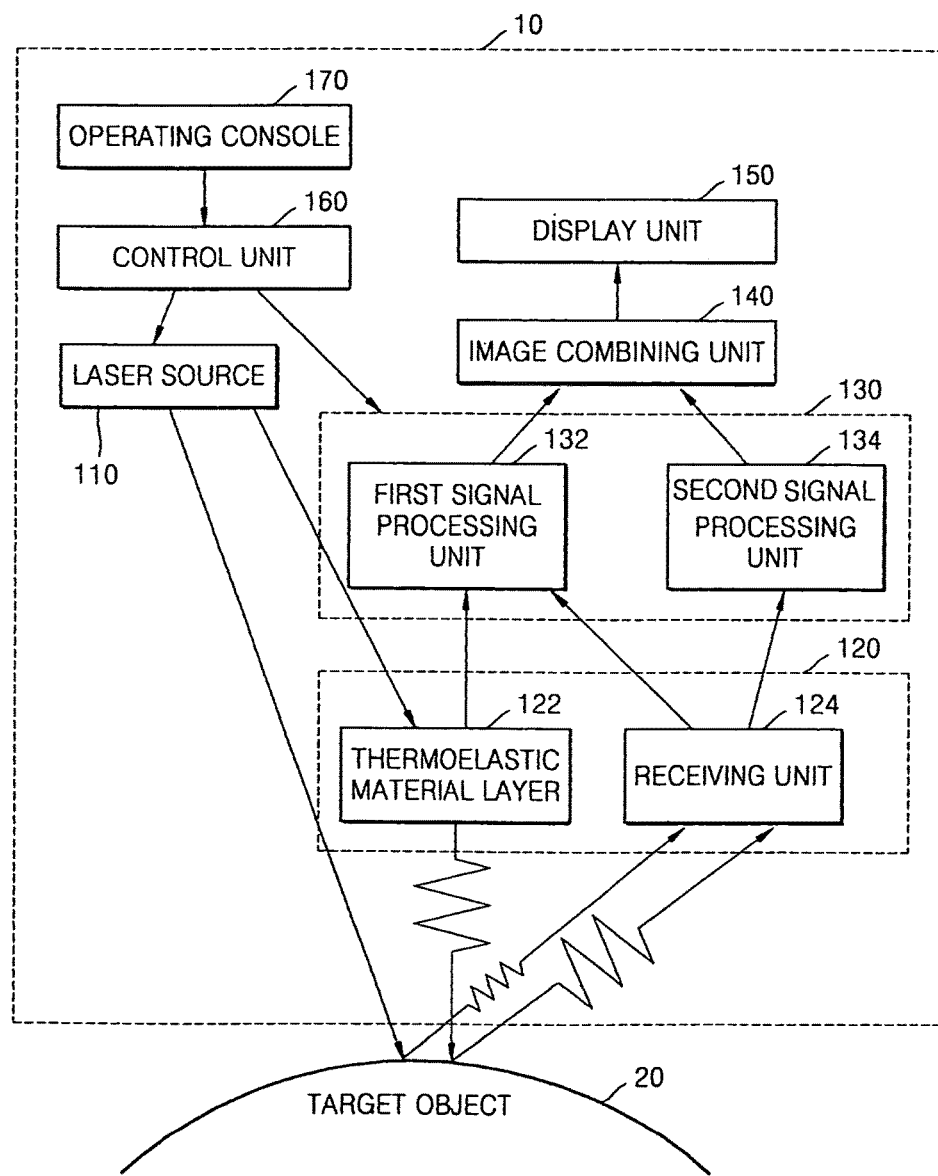
FIG. 3 is a schematic block diagram of a laser-induced ultrasonic wave apparatus, according to one or more embodiments.

FIG. 3 is a schematic block diagram of such a laser-induced ultrasonic wave apparatus 10, according to one or more embodiments.

As shown in FIG. 3, the laser-induced ultrasonic wave apparatus 10 (referred to hereinafter as an 'ultrasonic wave apparatus') may include a laser source 110 which irradiates a laser beam, or respectively split laser beams from the laser source 110, to a target object 20 and a thermoelastic material layer 122, with the thermoelastic material layer 122 converting a part of the laser beam to a first ultrasonic wave and irradiates the first ultrasonic wave to the target object 20, and a receiving unit 124 which receives an echo or reflection of the first ultrasonic wave from the target object 20 and a second ultrasonic wave generated by the target object 20 due to the direct irradiation of the laser beam to the target object 20. In one or more embodiments, the thermoelastic material layer 122 and the receiving unit 124 may be arranged in a single housing. For example, the thermoelastic material layer 122 and the receiving unit 124 may be arranged in an ultrasonic wave probe 120.

The laser source 110 may selectively generate laser beams with selectively different characteristics that induce ultrasonic waves from the target object 20 and the thermoelastic material layer 122. For example, the laser beams may be pulse laser beams, and a pulse width of the laser beams may be nano-sized or pico-sized.

Accordingly, the laser source 110 may be controlled to irradiate a laser beam to the target object 20 and the thermoelastic material layer 122. If the laser beam from the laser source is split into a laser beam irradiated to the target object 20 and a laser beam irradiated to the thermoelastic material layer 122, the split laser beams may have the same pulse width and the same pulse fluence as well as other characteristics. Alternatively, the split laser beams may be subsequently modified to have different pulse widths and/or different pulse fluences, or the laser source 110 may be controlled to irradiate respective different laser beams at different times with different pulse widths and/or different pulse fluences. A single laser source 110 may simultaneously respectively irradiate the split laser beams or the modified split laser beams to the target object 20 and the thermoelastic material layer 122. Since the target object 20 and the thermoelastic material layer 122 are spatially apart from each other, when the laser source 110 irradiates respective laser beams to the target object 20 and the thermoelastic material layer 122, the laser beams may be partially irradiated to the target object 20, partially irradiated to the thermoelastic material layer 122, and partially irradiated elsewhere, for example.

In one or more embodiments, when a laser beam from the laser source 110 is controlled to irradiate the target object 20 and the thermoelastic material layer 122 at different times, the laser source 110 may alternate between the irradiating the laser beam to the target object 20 and the irradiating the laser beam to the thermoelastic material layer 122. There may also be plural irradiations of the laser beam to either of the target object 20 or the thermoelastic material layer 122 before alternating to irradiate the laser beam to the target object 20 or the thermoelastic material layer 122 that was not the immediately previous irradiated target. For example, the laser source 110 may alternately irradiate a laser beam to the target object 20 and the thermoelastic material layer 122 by a period or by several periods. Particularly, in one or more embodiments, if it is impossible to induce ultrasonic waves from the target object 20 and the thermoelastic material layer 122 by using the same laser beam or the split laser beams with the same characteristics, e.g., based upon differently needed laser beam characteristics or a physical configuration of a respective embodiment, the laser source 110 may alternately irradiate a laser beam to the target object 20 and the thermoelastic material layer 122, respectively adjusting at least one of a pulse width and a pulse fluence of the laser. Accordingly, in one or more embodiments, ultrasonic waves may be generated by the target object 20 and the thermoelastic material layer 122 based upon irradiation of light energy from a single laser source 110.

When the laser source 110 is controlled so that a laser beam is wholly or partially irradiated to the thermoelastic material layer 122, a first ultrasonic wave is generated due to a thermoelastic phenomenon. The first ultrasonic wave is transmitted to the target object 20, where the incident first ultrasonic wave is partially absorbed by the target object 20 and the remainder of first ultrasonic wave is reflected by the target object 20. Next, the receiving unit 124 may receive an echo or reflected acoustic wave from the target object 20, that is, an echo or reflection of the first ultrasonic wave. In one or more embodiments, the thermoelastic material layer 122 may be formed of a material with excellent or satisfactory thermoelasticity, such as the example thermoelastic material layer used for the generation of the graphs of FIGS. 1A-1D, noting that alternate thermoelastic material layers having different relatively high absorption coefficient values may be equally used. In one or more embodiments, as only example, the thermoelastic material layer 122 may be formed of at least one of a metal, such as Cr, Ti, Au, Al, etc., a carbon-based material, such as carbon nanotubes (CNT), a semiconductor material, such as silicon, and a polymer material, such as polydimethylsiloxane (PDMS).

Furthermore, in one or more embodiments, a laser beam is directly irradiated from the laser source 110 to the target object 20. The target object 20 also generates a second ultrasonic wave due to a thermoelastic phenomenon. Since the thermoelastic material layer 122 and the target object 20 have different laser absorption coefficients, frequency bands and pressure magnitudes of the first ultrasonic wave generated by the thermoelastic material layer 122 and the second ultrasonic wave generated by the target object 20 may differ. Generally, the thermoelastic material layer 122 has a relatively greater absorption coefficient than the target object 20 resulting in a large pressure magnitude, while a pressure magnitude of the second ultrasonic wave generated by the target object 20 is smaller than that of the first ultrasonic wave generated by the thermoelastic material layer 122. In one or more embodiments, the second ultrasonic wave generated by the target object 20 is also received by the receiving unit 124.

In such an embodiment, the receiving unit 124 may receive the echo or reflected acoustic wave of the first ultrasonic wave and receive the second ultrasonic wave. Furthermore, the receiving unit 124 may include transducers which convert ultrasonic waves to electric signals. For example, the transducers may be piezoelectric micromachined ultrasonic wave transducers (pMUT) which convert ultrasonic waves to electric signals via oscillation. The piezoelectric material may be a piezoelectric ceramic which induces a piezoelectric phenomenon, or a composite piezoelectric material formed by combining the piezoelectric material with a polymer material. Furthermore, the transducers may be capacitive micromachined ultrasonic transducers (cMUT), magnetic micromachined ultrasonic transducers (mMUT), optical ultrasonic wave detectors, etc., noting that alternatives are also available.

In one or more embodiments, the converted electric signals, resulting from the conversion of the received echo or reflected acoustic wave of the first acoustic wave and the received second acoustic wave may be analog signals. The receiving unit 124 may generate a first electric signal, generated by converting a received echo or reflected acoustic wave of the first ultrasonic wave, to a first signal processing unit 132 and generate a second electric signal, generated by converting the received second ultrasonic wave, to a second signal processing unit 134. The receiving unit 124 may distinguish between the received acoustic waves by comparing at least one of frequency band, pressure magnitude, and time of the first ultrasonic wave to the received second ultrasonic wave, as only an example.

A signal processing unit 130 may generate an image or respective images by signal-processing the generated first and second electric signals. For example, the signal processing unit 130 may convert the first and/or second electric signals to respective first and second digital signals. Next, in consideration of locations of transducers and a focal point of the receiving unit 124, the signal processing unit 130 may generate a reception focus signal by reception-focusing the first and second digital signals. Accordingly, the signal processing unit 130 may form an image by using the reception focus signal. The signal processing unit 130 may perform various signal processes for forming an image, e.g., gain control, filtering, etc., on the reception focus signal.

The signal processing unit 130 may include the first signal processing unit 132 that controls the generation of a first image by processing first electric signals corresponding to the received echo or reflected acoustic wave of the first ultrasonic wave and the second signal processing unit 134 may generate a second image by processing second electric signals corresponding to the received second ultrasonic wave. As only an example, the first image may include a brightness (B) mode image, a Doppler (D) mode image, a color-Doppler (C) mode image, an elastic image, a 3-dimensional image, etc.

An image combining unit 140 may generate a third image by combining the first image with the second image. The first image and the second image may be combined with each other based on a particular point of a target object, for example. Though combination of such first and second images corresponding to one or more embodiments is not known, since general techniques for combining a plurality of images are well known in the art, further detailed description thereof is omitted. Next, a display unit 150 may be controlled to display the third image generated by the image combining unit 140. If necessary, the display unit 150 may be controlled to display the first image or the second image. Alternatively, the display unit 150 may be controlled to simultaneously display at least two of the first through third images. Depending on embodiment, if the display unit 150 displays the first image or the second image, a process of the image combining unit 140 may be bypassed.

Furthermore, a control unit 160 controls one or more of the aforementioned components of the ultrasonic wave apparatus 10, e.g., according to user instructions input via an operating console 170, or based upon an automated plan. The operating console 170 may receive data input by the user. As only examples, the operating console 170 may include a control panel, a keyboard, a mouse, a touch pad or screen, etc., and the operating console 170 may also be physically separated from one or more remaining components of the laser-induced ultrasonic wave apparatus 10, such as a portable computing device, such as a tablet computer.

Accordingly, in one or more embodiments, different ultrasonic waves may be generated from irradiation of selectively different laser beams from a same laser in the ultrasonic wave apparatus 10, with the single laser being controlled to irradiate both the thermoelastic material layer and target object, and with the irradiation to both the thermoelastic material layer and target object being controlled to occur simultaneously. For example, in one or more embodiments, a laser beam generated by the laser may be split into two laser beams, i.e., thereby duplicating the laser beam generated by the laser, and the two laser beams may be respectively directed to the thermoelastic material layer and the target object simultaneously. In one or more embodiments, the respectively generated ultrasonic waves may also be received and converted to respective electrical signals at the same time, e.g., by the receiving unit. Further, in one or more embodiments, as noted above, the pulse width and fluence of the laser beam may be selectively controlled based upon properties of the target object. Similarly, a center frequency and bandwidth of the acoustic wave generated by the thermoelastic material layer may be changed by selectively changing the pulse width, e.g., with an increase in the pulse width resulting in an increase in the wavelength of the acoustic wave generated by the thermoelastic material layer.

Figure 4:
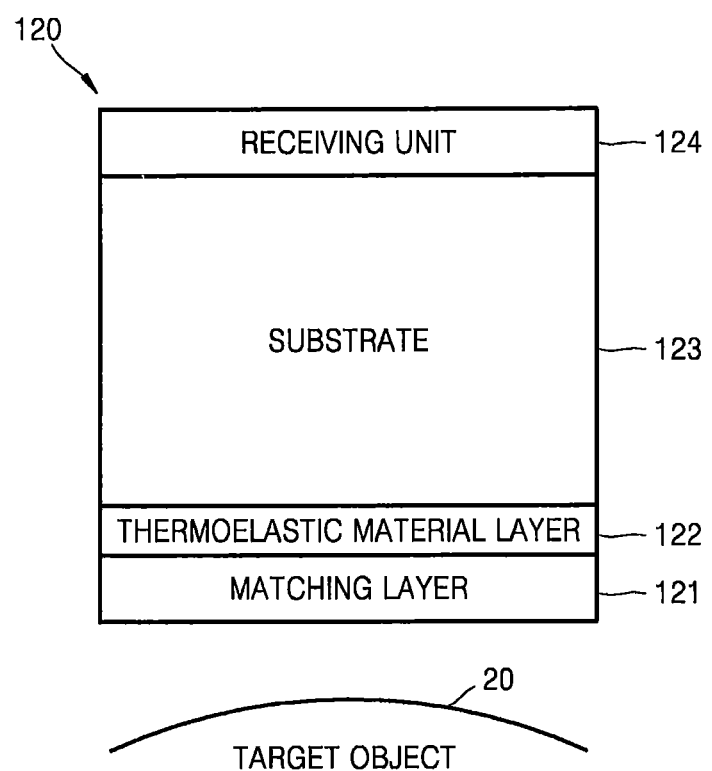
FIG. 4 is a diagram illustrating a combination relationship between a receiving unit and a thermoelastic material layer, such as shown in FIG. 3, according to one or more embodiments.

FIG. 4 is a diagram illustrates a configured combination of the receiving unit 124 and the thermoelastic material layer 122, such as illustrated in FIG. 3, according to one or more embodiments.

As shown in FIG. 4, the thermoelastic material layer 122 and the receiving unit 124 may be arranged in a single ultrasonic wave probe 120. For example, in a direction from the target object 20 to the ultrasonic wave probe 120, the ultrasonic wave probe may be configured as illustrated in the order of the thermoelastic material layer 122 and the receiving unit 124. Therefore, in such an embodiment, when the laser source 110 irradiates a laser beam to the thermoelastic material layer 122, the potential receiving of the laser beam by the receiving unit 124 may be minimized.

Furthermore, in one or more embodiments, a matching layer 121, which may match a sound impedance of an ultrasound wave to a sound impedance of the target object 20, may be arranged on a front or illustrated bottom surface of the thermoelastic material layer 122. The matching layer 121 may change sound impedance of the first ultrasonic wave generated by the thermoelastic material layer 122 in stages, for example, such that a sound impedance of the first ultrasonic wave becomes close to that of the target object 20. Here, the front or bottom surface of the thermoelastic material layer 122 may refer to a surface of the thermoelastic material layer 122 that is closest to the target object 20 while the first ultrasonic wave is being irradiated to the target object 20, whereas a rear surface of the thermoelastic material layer 122 may refer to the surface opposite to the front surface, as illustrated in FIG. 4 as being adjacent to the front or bottom surface of substrate 123. The matching layer 121 may be formed in a linear shape on the front surface of the thermoelastic material layer 122, noting that embodiments are not limited thereto. When manufactured, the matching layer 121 may be formed on a portion of the thermoelastic material layer 122, with the matching layer 121 having a single layer structure or a multi-layer structure. The matching layer 121 may be formed of polydimethylsiloxane (PDMS), as only an example.

Furthermore, the substrate 123 may be arranged between the thermoelastic material layer 122 and the receiving unit 124. The substrate 123 supports the receiving unit 124 and the thermoelastic material layer 122 to form a single body and may be formed of a material with high laser transmissivity, so that a laser beam may irradiate the thermoelastic material layer 122 through the substrate 123. Furthermore, a material constituting the substrate 123 may also have high ultrasonic wave transmissivity, so that the received echo or reflected acoustic wave of the first ultrasonic wave and the received second ultrasonic wave traverse through the substrate 123 are capable of being received by the receiving unit 124, e.g., without a loss. The substrate 123 may be formed of quartz, fused silica, glass, etc., as only examples.

Furthermore, to minimize loss of ultrasonic waves received by the receiving unit 124, a thickness of the thermoelastic material layer 122 may be smaller than expected wavelengths of the received echo or reflected acoustic wave of the first ultrasonic wave and the received second ultrasonic wave. For example, the thermoelastic material layer 122 may be formed as a thin-film and may have a thickness from about 10 nm to about 100 nm. Therefore, in one or more embodiments, even if the received echo or reflected acoustic wave of the first ultrasonic wave transitions through the thermoelastic material layer 122, the properties of the echo or reflected wave of the first ultrasonic wave may not be significantly altered by the thermoelastic material layer 122.

FIGS. 5A through 5D are diagrams illustrating alternative configurations of example combinations of a receiving unit and a thermoelastic material layer, according to one or more embodiments.

Figure 5A:
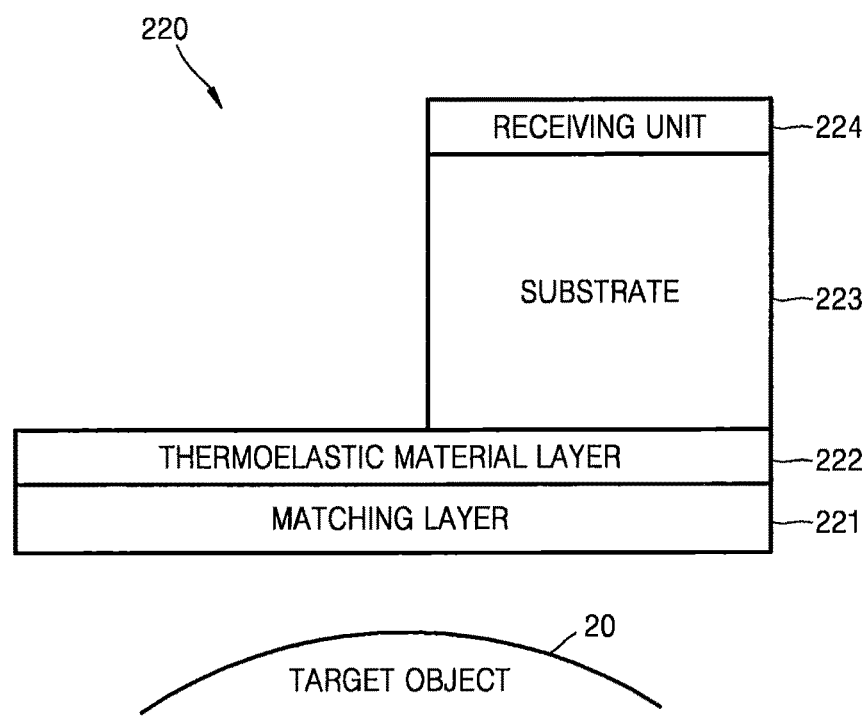
FIGS. 5A through 5D are diagrams illustrating different example combination relations between a receiving unit and a thermoelastic material layer, such as shown in FIG. 3, according to one or more embodiments.
Figure 5B:
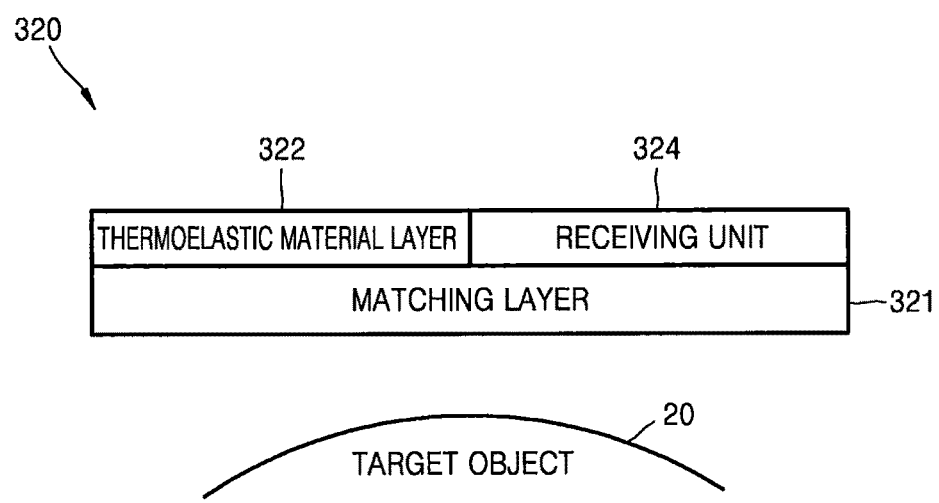
Figure 5C:
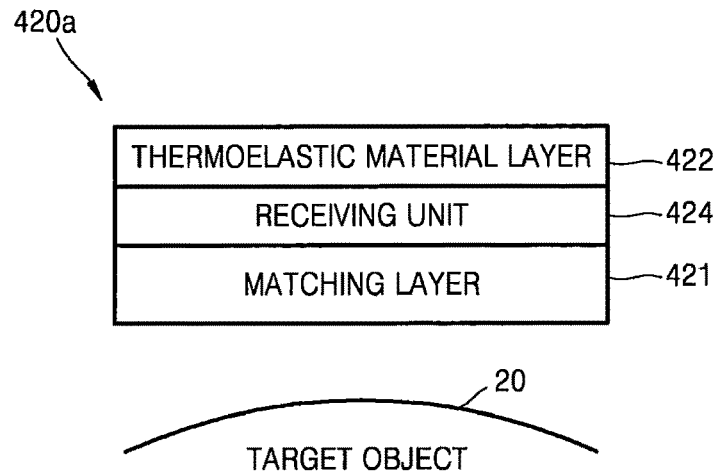

As shown in FIG. 5A, again in the direction of the target object 20 to the ultrasonic wave probe 220, a substrate 223 and a receiving unit 224 may be arranged below a portion of a matching layer 221 and a portion of a thermoelastic material layer 222. In this case again, the effects of a laser beam on the receiving unit 224 may be minimized. Alternatively, as shown in FIG. 5B, in the direction of the target object 20 to the ultrasonic wave probe 320, a thermoelastic material layer 322 and a receiving unit 324 may be arranged side-by-side below a matching layer 321. In this case, loss of ultrasonic waves due to the thermoelastic material layer 322 may be minimized.

Figure 5D:
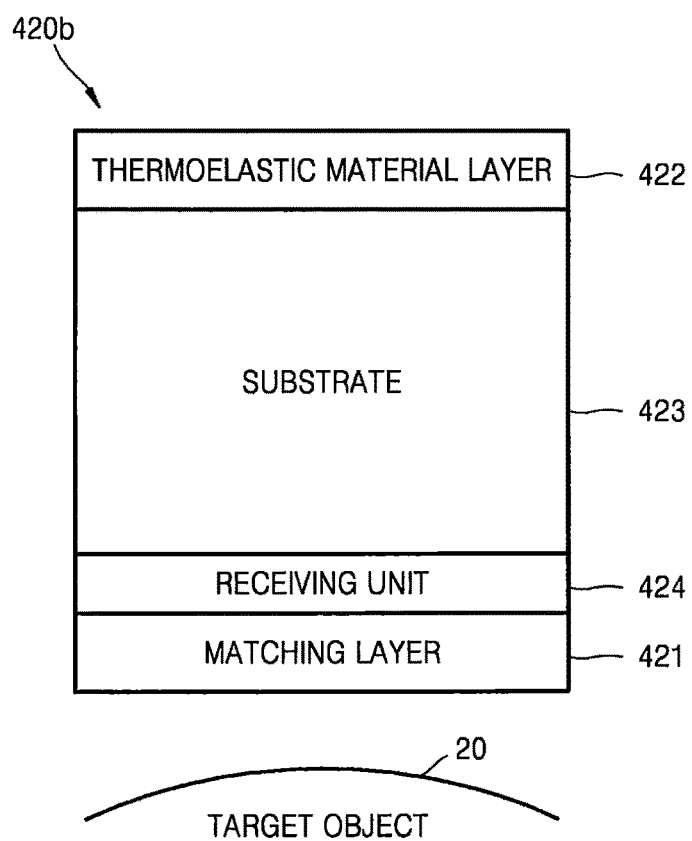

Alternatively, as shown in FIG. 5C, again in the direction of the target object 20 to the ultrasonic wave probe 420*a* along the direction in which the echo or reflected acoustic wave of the first ultrasonic wave propagates, an ultrasonic wave probe 420*a* may be configured so a receiving unit 424 and a thermoelastic material layer 422 are arranged in the illustrated order, with the thermoelastic material layer 422 being formed below the receiving unit 424, and the receiving unit 424 being formed below the matching layer 421. Alternatively, as shown in FIG. 5D, in the direction of the target object 20 to the ultrasonic wave probe 420*b*, a substrate 423 may be arranged between the receiving unit 424 and the thermoelastic material layer 422 of FIG. 5C.

Figure 6:
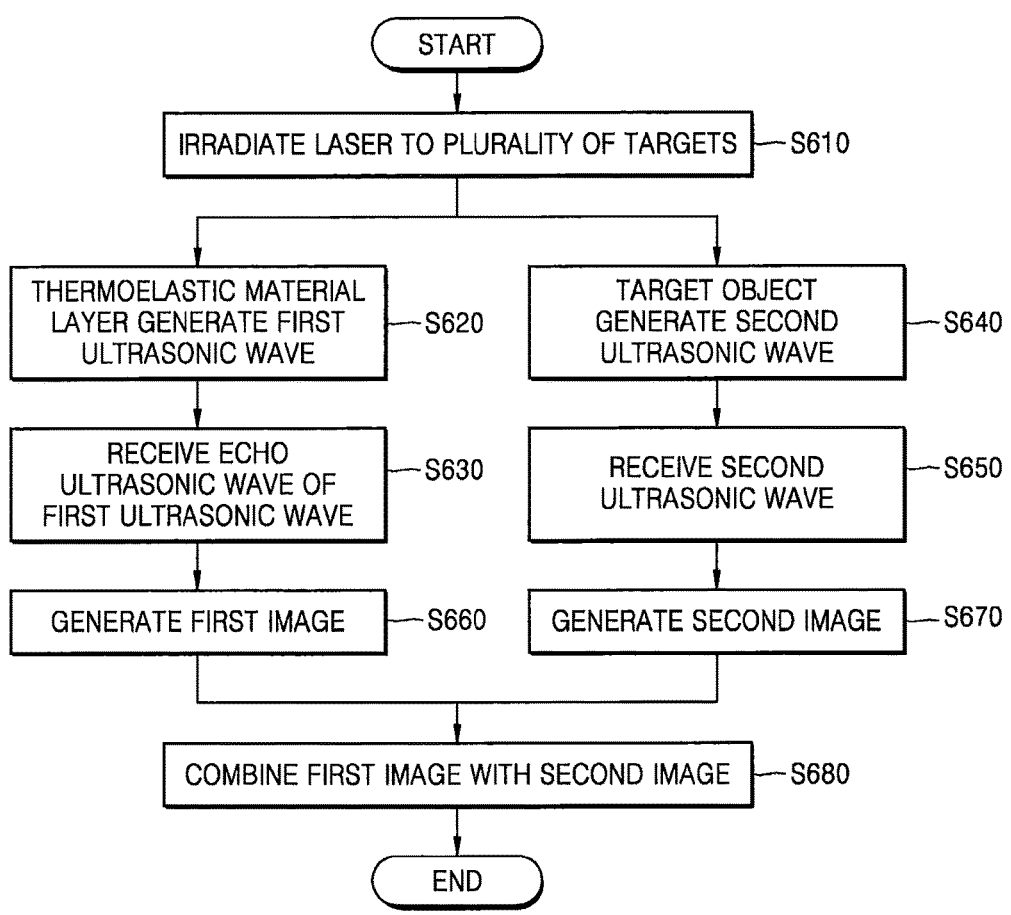
FIG. 6 is a flowchart illustrating a method of generating an image by using laser-induced ultrasonic waves, according to one or more embodiments.

FIG. 6 is a flowchart illustrating a method of generating an image by using laser-induced ultrasonic waves, according to one or more embodiments. Below, references to components of the laser-induced ultrasonic wave apparatus 10 of FIG. 3 will be used to explain the operations of FIG. 6, though method embodiments are not limited to a particular arrangement or configuration of one or more of such components illustrated in FIG. 3.

Referring to FIG. 6, the laser source 110 may irradiate laser beams to the target object 20 and the thermoelastic material layer 122 (operation S610). The laser beams generated by the laser source 110 may be pulse laser beams. The laser source 110 may irradiate laser beams to the target object 20 and the thermoelastic material layer 122 simultaneously or may irradiate a laser beam to the target object 20 and the thermoelastic material layer 122 separately, e.g., in an alternating manner.

When a laser beam irradiates the thermoelastic material layer 122, the thermoelastic material layer 122 generates a first ultrasonic wave (operation S620). The generated first ultrasonic wave is transmitted to the target object 20. Here, the receiving unit 124 may receive the echo or reflection acoustic wave of the first ultrasonic wave from the target object 20 (operation S630).

Furthermore, when a laser beam is directly irradiated to the target object 20, the target object 20 generates a second ultrasonic wave (operation S640). When the thermoelastic material layer 122 and the target object 20 have different ultrasonic wave absorption coefficients, ultrasonic wave reflection coefficients, specific heats, and/or thermal expansion coefficients, the target object 20 generates the second ultrasonic wave of which at least one of frequency band, pressure magnitude, and velocity is different from corresponding characteristics of the first ultrasound wave. Here, the receiving unit 124 may receive the second ultrasonic wave transmitted from the target object 20 (operation S650).

The receiving unit 124 may receive the echo or reflected acoustic wave of the first ultrasonic wave and receive the second ultrasonic wave, transduce and convert the received acoustic waves to digital signals, and apply the digital signals to the signal processing unit 130. In the signal processing unit 130, the first signal processing unit 132 may generate a first image by processing first electric signals corresponding to the received echo or reflected acoustic wave of the first ultrasonic wave (operation S660) and the second signal processing unit 134 may generate a second image by processing second electric signals corresponding to the received second ultrasonic wave (operation S670). Depending on embodiment, the first image and the second image may further be applied to the image combining unit 140.

The image combining unit 140 may generate a third image by combining the first image with the second image (operation S680).

As described above, since different types of ultrasound waves may be generate,d by using a single laser source, an image for functional analysis and an image for anatomical analysis may be obtained together and simultaneously. Furthermore, compared to conventional ultrasonic wave devices that transduce electric signals to ultrasonic waves, e.g., using piezoelectric devices for generating respective acoustic waves having different center frequencies, a configuration of a laser-induced ultrasonic wave apparatus, according to one or more embodiments, for ultrasonic wave transmission may be more simple, efficient, and easier to manufacture. Furthermore, according to one or more embodiments, the use of signal/acoustic wave transducers may be used only in the receiving unit's reception and conversion to electric signals of received ultrasonic waves. Thus such transducers used only in the reception and conversion of ultrasonic waves may be designed so reception properties of the transducers may be improved over conventional approaches where wavelengths of acoustic waves generated by such a transducer for transmission to a target object are ultimately similar to acoustic waves generated and transmitted by an irradiated target object. As another example, transducers may be designed by using a material which features high efficiency for converting ultrasonic waves to electric signals and broadband frequency properties that may not have been available in conventional systems because transducers are used to generate the acoustic wave that is transmitted to the target object.

Furthermore, in one or more embodiments, ultrasonic waves with different properties may be generated by merely changing characteristics of the laser beam, e.g., according to the type of the target object, so with differing configuration and method approach embodiments it is easier to control ultrasonic waves as compared to the conventional generation of ultrasonic waves using a transducer to generate acoustic waves. For example, as noted above, a conventional ultrasonic wave apparatus using piezoelectric devices must uses plural different piezoelectric devices according to a type of a target object, e.g., to generate different acoustic waves with distinct center frequencies. Rather, in one or more embodiments a laser-induced ultrasonic wave apparatus may adjust frequencies of ultrasonic waves by merely changing characteristics of a single laser beam.

As described above, according to the one or more of the above embodiments, the laser-induced ultrasonic wave apparatus may generate ultrasonic waves with different properties according to materials to which a laser beam from a laser source is incident, so an image for functional analysis and an image for anatomical analysis may be obtained together.

Furthermore, in one or more embodiments, the laser-induced ultrasonic wave apparatus may generate ultrasonic waves by using a single laser beam, so an image for anatomical analysis and an image for functional analysis may be generated simultaneously, resulting in a simplified apparatus and method compared to a conventional ultrasonic wave devices that generate ultrasonic waves by using electric signal/acoustic wave transducers.

Furthermore, in one or more embodiments, ultrasonic waves may be generated by adjusting characteristics of a single laser beam based on a type of a target object that is to be irradiated by the laser beam and that is to be transmitted an acoustic wave generated by the laser beam irradiation of the thermoelastic material layer, resulting in an easier and simpler approach to adjusting ultrasonic waves as compared to a conventional generation of ultrasonic waves necessitating using one or more electric signal/acoustic wave transducers.

In one or more embodiments, any apparatus, system, and unit descriptions herein may include one or more hardware devices or hardware processing elements. For example, in one or more embodiments, any described apparatus, system, and unit may further include one or more desirable memories, and any desired hardware input/output transmission devices. Further, the term apparatus should be considered synonymous with elements of a physical system, not limited to a single device or enclosure or all described elements embodied in single respective enclosures in all embodiments, but rather, depending on embodiment, is open to being embodied together or separately in differing enclosures and/or locations through differing hardware elements.

In addition to the above described embodiments, embodiments can also be implemented through computer readable code/instructions in/on a non-transitory medium, e.g., a computer readable medium, to control at least one processing device, such as a processor or computer, to implement any above described embodiment. The medium can correspond to any defined, measurable, and tangible structure permitting the storing and/or transmission of the computer readable code.

The media may also include, e.g., in combination with the computer readable code, data files, data structures, and the like. One or more embodiments of computer-readable media include: magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Computer readable code may include both machine code, such as produced by a compiler, and files containing higher level code that may be executed by the computer using an interpreter, for example. The media may also be any defined, measurable, and tangible distributed network, so that the computer readable code is stored and executed in a distributed fashion. Still further, as only an example, the processing element could include a processor or a computer processor, and processing elements may be distributed and/or included in a single device. The processing element may be a specially designed computing device to implement one or more of the embodiments described hererin.

The computer-readable media may also be embodied in at least one application specific integrated circuit (ASIC) or Field Programmable Gate Array (FPGA), as only examples, which execute (processes like a processor) program instructions.

While aspects of the present invention has been particularly shown and described with reference to differing embodiments thereof, it should be understood that these embodiments should be considered in a descriptive sense only and not for purposes of limitation. Descriptions of features or aspects within each embodiment should typically be considered as available for other similar features or aspects in the remaining embodiments. Suitable results may equally be achieved if the described techniques are performed in a different order and/or if components in a described system, architecture, device, or circuit are combined in a different manner and/or replaced or supplemented by other components or their equivalents.

Thus, although a few embodiments have been shown and described, with additional embodiments being equally available, it would be appreciated by those skilled in the art that changes may be made in these embodiments without departing from the principles and spirit of the invention, the scope of which is defined in the claims and their equivalents.

What is claimed is:

1. A laser-induced ultrasonic wave apparatus, the apparatus comprising:
   a laser source configured to irradiate a target object and a thermoelastic material with a laser beam;
   the thermoelastic material configured to be spatially apart from the target object, configured to generate a first acoustic wave based upon irradiation of the thermoelastic material by the laser beam, and configured to transmit the first acoustic wave to the target object;
   a transducer configured to transduce acoustic waves into electric signals, the transducer including at least one piezoelectric micromachined ultrasonic transducer (pMUT), capacitive micromachined ultrasonic transducer (cMUT), or magnetic micromachined ultrasonic transducer (mMUT); and
   a substrate between the thermoelastic material and the transducer in a single probe such that the single probe includes the thermoelastic material, the substrate, and the transducer,
   wherein the transducer is further configured to
      receive an echo acoustic wave of the first acoustic wave, as reflected from the target object through the substrate, and transduce the echo acoustic wave into first electric signals, and
      receive a second acoustic wave generated in the target object by irradiation of the target object by the laser beam from the target object through the substrate and transduce the second acoustic wave into second electric signals.

2. The laser-induced ultrasonic wave apparatus of claim 1, further comprising:
   at least one image processor configured to simultaneously generate a first image based upon the received second acoustic wave and a second image based upon the received echo acoustic wave;
   wherein the at least one image processor is further configured to generate the first image as a photoacoustic image for functional analysis of the target object, and
   wherein the at least one image processor is further configured to generate the second image as an anatomical image for acoustic analysis of at least the target object.

3. The laser-induced ultrasonic wave apparatus of claim 2, further comprising:
   a user interface;
   a display; and
   a controller configured to control the at least one image processor to output at least one of the first image or the second image to the display based upon a user input detected by the user interface.

4. The laser-induced ultrasonic wave apparatus of claim 1, further comprising:
   a controller configured to selectively change a pulse width of the laser beam based upon properties of the target object;
   wherein the thermoelastic material is further configured to generate respective acoustic waves with different wavelengths based upon the selectively changed pulse width of the laser beam.

5. The laser-induced ultrasonic wave apparatus of claim 1, further comprising:

a controller configured to selectively change a pulse width of the laser beam based upon properties of the target object;

wherein the thermoelastic material is further configured to generate respective acoustic waves with different pressure magnitudes based upon the selectively changed pulse width of the laser beam.

6. The laser-induced ultrasonic wave apparatus of claim 1, further comprising:

a controller configured to selectively change a fluence of the laser beam based upon properties of the target object;

wherein the thermoelastic material is further configured to generate respective acoustic waves with different pressure magnitudes based upon the selectively changed fluence of the laser beam.

7. The laser-induced ultrasonic wave apparatus of claim 1, wherein the laser-induced ultrasonic wave apparatus is configured to split the laser beam into a first laser beam and a second laser beam that both maintain same characteristics as the laser beam, and wherein the first laser beam is optically directed to irradiate at least a portion of the target object distinct from the second laser beam being optically directed to irradiate at least a portion of the thermoelastic material.

8. The laser-induced ultrasonic wave apparatus of claim 1, wherein the laser source simultaneously irradiates at least a portion of the target object with the laser beam and at least a portion of the thermoelastic material with the laser beam.

9. The laser-induced ultrasonic wave apparatus of claim 1, further comprising:

a controller configured to control the laser source to selectively irradiate only the target object with the laser beam during a first time period, and configured to irradiate only the thermoelastic material with the laser beam during a second time period;

wherein the first time period and the second time period are sequential in time and occur while the transducer is enabled to receive and transduce the echo acoustic wave and the second acoustic wave.

10. The laser-induced ultrasonic wave apparatus of claim 9, wherein the controller is further configured to controls the laser source to generate the laser beam to have respectively different characteristics during the first time period than during the second time period based upon properties of the target object.

11. The laser-induced ultrasonic wave apparatus of claim 1, further comprising:

a controller configured to selectively change characteristics of the laser beam to change a center frequency of the first acoustic wave generated by the thermoelastic material based upon properties of the target object.

12. The laser-induced ultrasonic wave apparatus of claim 1, wherein the thermoelastic material is selected so that an absorption rate of the target object is smaller than an absorption rate of the thermoelastic material.

13. The laser-induced ultrasonic wave apparatus of claim 1, wherein a pulse width of the laser beam is nano-sized or pico-sized.

14. The laser-induced ultrasonic wave apparatus of claim 1, wherein the thermoelastic material is formed of at least one of a metal, a semiconductor material, a carbon-based material, or a polymer material.

15. The laser-induced ultrasonic wave apparatus of claim 1, wherein the thermoelastic material is formed as a thin-film having a thickness less than respective wavelengths of the echo acoustic wave reflected from the target object and the second acoustic wave propagating from the target object.

16. The laser-induced ultrasonic wave apparatus of claim 1, wherein the thermoelastic material and the transducer are embodied together as the single probe.

17. The laser-induced ultrasonic wave apparatus of claim 16, wherein the thermoelastic material and the transducer are arranged in the single probe in a configuration so that when the laser beam is incident on the single probe, the thermoelastic material is enabled to be irradiated by the laser beam, and incidence of the laser beam on the transducer is minimized.

18. The laser-induced ultrasonic wave apparatus of claim 16, wherein the thermoelastic material and the transducer are arranged in the single probe so that the first acoustic wave generated by the thermoelastic material propagates through the transducer before propagating to the target object.

19. The laser-induced ultrasonic wave apparatus of claim 1, wherein the laser source is further configured to irradiate the target object and the thermoelastic material simultaneously with the laser beam.

20. The laser-induced ultrasonic wave apparatus of claim 1, further comprising:

a first signal processing processor configured to generate a first image based upon electric signals derived from the received echo acoustic wave;

a second signal processing processor configured to generate a second image based upon electric signals derived from the received second acoustic wave; and an image combining processor configured to generate a third image by combining the first image and the second image.

21. A laser-induced ultrasonic wave method, the method comprising:

irradiating a target object and a thermoelastic material with a laser beam;

receiving and transducing, at a transducer configured to transduce acoustic waves into electric signals, an echo acoustic wave, from the target object, as a reflection of a first acoustic wave transmitted to the target object from the thermoelastic material upon the thermoelastic material being irradiated by the laser beam, the transducer including at least one piezoelectric micromachined ultrasonic transducer (pMUT), capacitive micromachined ultrasonic transducer (cMUT), or magnetic micromachined ultrasonic transducer (mMUT); and receiving and transducing, at the transducer, a second acoustic wave generated in the target object upon the target object being irradiated by the laser beam from the target object, wherein a substrate is between the thermoelastic material and the transducer in a single probe such that the single probe includes the thermoelastic material, the substrate, and the transducer and the echo acoustic wave and second acoustic wave are received by the transducer through the substrate, the single probe being separate from the target object such that the thermoelastic material is between the substrate and the target object, such that the laser beam, the first acoustic wave, and the second acoustic wave traverse through the substrate between the transducer and the thermoelastic material.

22. The laser-induced ultrasonic wave method of claim 21, further comprising simultaneously generating a first image based on the received second acoustic wave and a second image based on the received echo acoustic wave, wherein the first image is generated to be a photoacoustic image for functional analysis of the target object and the second image is generated to be an anatomical image for acoustic analysis of at least the target object.

23. The laser-induced ultrasonic wave method of claim 22, further comprising selectively displaying at least one of the first image and the second image based upon a user input to a user interface.

24. The laser-induced ultrasonic wave method of claim 21, wherein the thermoelastic material is selected so that when the target object is a tissue within a human body, an absorption rate of the target object is smaller than an absorption rate of the thermoelastic material.

25. The laser-induced ultrasonic wave method of claim 21, wherein the thermoelastic material is formed as a thin-film having a thickness less than respective wavelengths of the echo acoustic wave and the second acoustic wave propagating from the target object.

26. The laser-induced ultrasonic wave method of claim 21, wherein the thermoelastic material and the transducer, performing the receiving of the echo acoustic wave and the second acoustic wave, are embodied together as a single probe element.

27. The laser-induced ultrasonic wave method of claim 21, wherein the target object and the thermoelastic material are simultaneously irradiated with the laser beam.

28. The laser-induced ultrasonic wave method of claim 21, further comprising:
generating a first image based on electric signals derived from the received echo acoustic wave;
generating a second image based on electric signals derived from the received second acoustic wave; and
generating a third image by combining the first image and the second image.

* * * * *